United States Patent [19]
Chang et al.

[11] Patent Number: 5,762,764
[45] Date of Patent: Jun. 9, 1998

[54] PURIFICATION OF ACETONE

[75] Inventors: Te Chang, West Chester; Vijai P. Gupta, Berwyn, both of Pa.

[73] Assignee: Arco Chemical Technology, L.P., Greenville, Del.

[21] Appl. No.: 705,378

[22] Filed: Aug. 29, 1996

[51] Int. Cl.$^6$ .................. B01D 3/40; C07C 49/08
[52] U.S. Cl. .................. 203/52; 203/68; 203/69; 203/70; 568/411
[58] Field of Search .................. 203/68, 70, 69, 203/52; 568/411

[56] References Cited

U.S. PATENT DOCUMENTS

| | | | |
|---|---|---|---|
| 2,528,761 | 11/1950 | Lake et al. | 203/69 |
| 2,617,757 | 11/1952 | Michael | 203/68 |
| 2,624,699 | 1/1953 | Joris . | |
| 2,906,675 | 9/1959 | Hall et al. . | |
| 2,906,676 | 9/1959 | Bewley et al. . | |
| 3,182,006 | 5/1965 | Fruhwirth | 203/68 |
| 3,668,256 | 6/1972 | Brundege . | |
| 4,012,289 | 3/1977 | Haskell | 203/62 |
| 4,113,780 | 9/1978 | Strehlke et al. | 203/63 |
| 4,329,510 | 5/1982 | Uno et al. . | |
| 4,444,624 | 4/1984 | Erpenbach et al. | 568/411 |
| 4,501,645 | 2/1985 | Berg et al. | 203/56 |
| 4,551,207 | 11/1985 | Berg et al. | 568/411 |
| 4,584,063 | 4/1986 | Berg et al. . | |
| 4,620,901 | 11/1986 | Berg et al. . | |
| 4,931,145 | 6/1990 | Berg | 203/69 |
| 5,084,142 | 1/1992 | Berg et al. | 203/60 |
| 5,085,739 | 2/1992 | Berg et al. | 203/57 |
| 5,567,853 | 10/1996 | Gupta . | |

*Primary Examiner*—Virginia Manoharan
*Attorney, Agent, or Firm*—Stephen D. Harper; William C. Long

[57] ABSTRACT

Close boiling hydrocarbon impurities are separated from acetone by extractive distillation using a $C_9$–$C_{14}$ alkane and/or a $C_8$–$C_{12}$ aromatic hydrocarbon extractive distillation solvent.

4 Claims, 1 Drawing Sheet

PURIFICATION OF ACETONE

BACKGROUND OF THE INVENTION

1. Field of the Invention

The present invention relates to the separation of acetone from close boiling hydrocarbon impurities by extractive distillation with a $C_9$–$C_{14}$ alkane and/or a $C_8$–$C_{12}$ aromatic hydrocarbon extractive distillation agent.

2. Description of the Prior Art

Methyl tertiary butyl ether (MTBE) is an important industrial chemical useful, for example, as a fuel additive. In commercial practice, MTBE is produced by the reaction of methanol with isobutylene and/or tertiary butyl alcohol. An important source of the isobutylene and/or tertiary butyl alcohol is from the Oxirane process which is widely practiced commercially for the coproduction of propylene oxide and tertiary butyl alcohol. The isobutylene and/or tertiary butyl alcohol produced from the Oxirane process tends to also contain oxygenated impurities such as acetone, methanol and aldehydes, as well as close boiling hydrocarbons.

While the bulk of the acetone can be separated by distillation, the resultant acetone fraction is contaminated with methanol which forms an azeotrope with acetone, as well as with close boiling aldehydes such as butyraldehydes, with acids such as butyric acid, with impurities such as methyl ethyl ketone, tertiary butyl alcohol, MTBE and the like which form azeotropes with water, and with close boiling hydrocarbons such as $C_8$ hydrocarbons and light aromatics such as benzene.

Co-pending application Ser. No. 08/526,151 filed Feb. 17, 1995 now U.S. Pat. No. 5,567,853 issued Oct. 22, 1996 provides a process for the separation of methanol and aldehyde impurities from acetone. However, in many instances the acetone remains contaminated with close boiling hydrocarbons which cannot be removed by conventional distillation or by the procedures of said U.S. Pat. No. 5,567,853 or other conventional procedures.

SUMMARY OF THE INVENTION

In accordance with the present invention, acetone containing close boiling hydrocarbon impurities can be readily purified by extractive distillation with a $C_9$–$C_{14}$ alkane and/or a $C_8$–$C_{12}$ aromatic hydrocarbon extractive distillation solvent.

DETAILED DESCRIPTION

Figure 1:
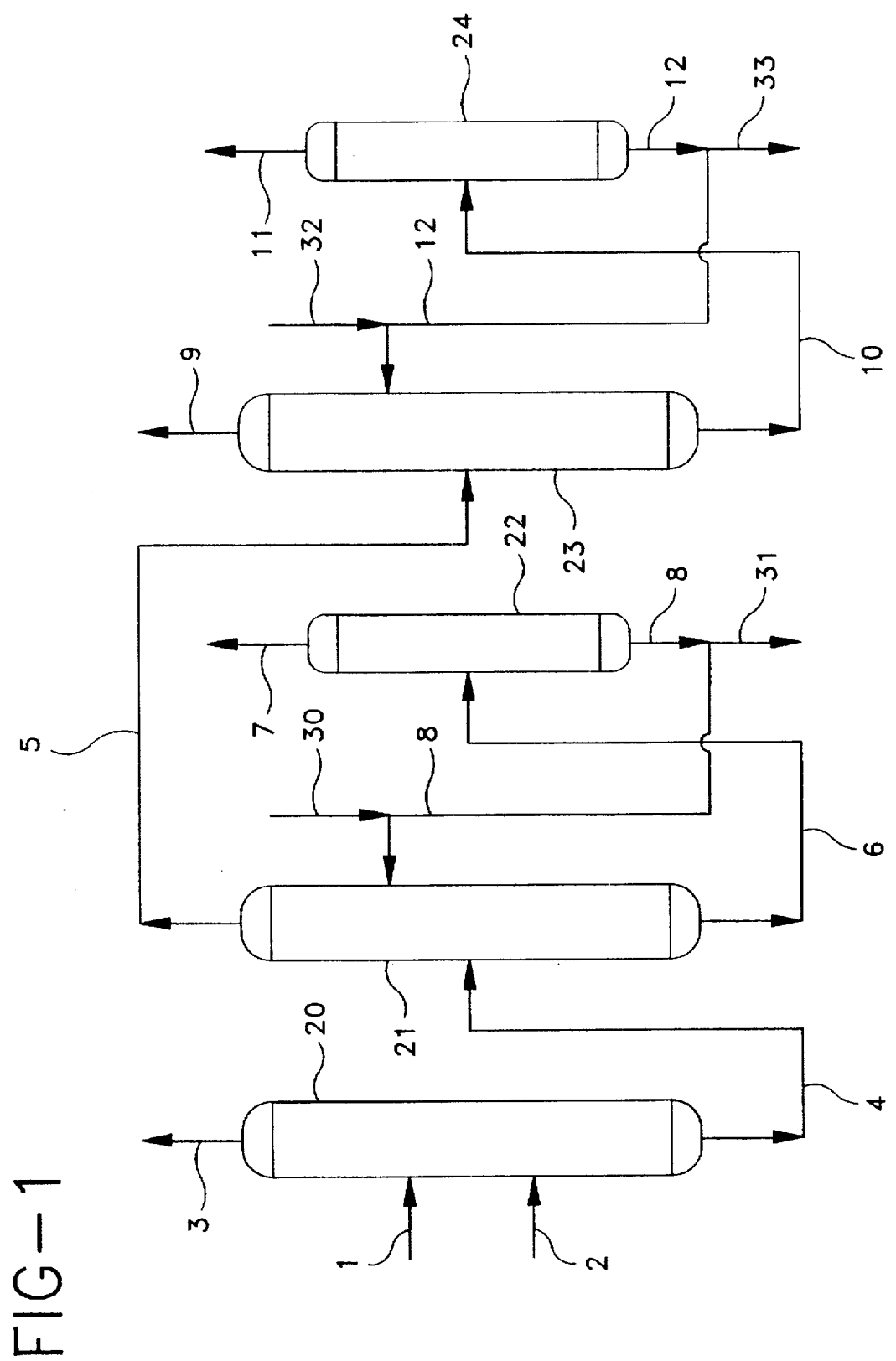
FIG. 1 is a schematic representation of an embodiment of the invention.

The invention can, perhaps, best be described with reference to the attached drawing. Referring to the drawing, impure acetone produced in the Oxirane propylene oxide and tertiary butyl alcohol process is introduced via line 1 to distillation zone 20. The impure acetone generally comprises by weight about 70 to 90% acetone, 3 to 18% methanol, 0.01 to 3% aldehyde, and the balance impurities such as methyl ethyl ketone (MEK), tertiary butyl alcohol (TBA) and MTBE as well as about 0.1 to 3.0% close boiling hydrocarbons having 7 to 9 carbon atoms. Also introduced via line 2 to zone 20 in combination with the impure acetone is a solution of an alkali metal compound such as NaOH in a polar solvent such as water or lower glycol.

In distillation column 20, light impurities are distilled overhead via line 3 from the impure acetone and the alkali metal compound solution which is removed via line 4 and passed to extractive distillation column 21. In column 21, the mixture from column 20 is extractively distilled using ethylene glycol or monopropylene glycol as extractive distillation solvent. The bulk of the solvent is recycled to column 21 via line 8 from stripper 22, with make-up added via line 30. In columns 20 and 21, the alkali metal compound catalyzes the polymerization of aldehyde impurities to higher boiling materials, and a bottoms stream comprised of the basic material, glycol, and the polymerized higher boiling impurities is removed via line 8. Most of this bottoms stream is recycled via line 8 to distillation zone 21 with a portion being purged via line 31.

The overhead from stripper 22 is comprised of the separated methanol, water and other organics and may be further worked up.

The overhead from extractive distillation column 21 is comprised of acetone and close boiling hydrocarbons and, in accordance with the invention, this stream passes via line 5 to extractive distillation column 23 for separation of the acetone from close boiling hydrocarbons by the extractive distillation procedure of this invention.

The extractive distillation solvent used is a $C_9$–$C_{14}$ and/or a $C_8$–$C_{12}$ aromatic hydrocarbon, preferably a $C_{10}$–$C_{14}$ alkane. A typical solvent to acetone feed weight ratio is from 0.2–5 to maintain extractive distillation solvent concentration on the distillation trays at a level to be effective. The reflux to distillate weight ratio should be around 0.5–4 and the solvent feed location should be at least a few trays below the top to effectively avoid solvent contamination of product acetone overhead. The acetone feed tray should be located many trays below the solvent feed tray to provide sufficient extractive distillation stages to allow the solvent to completely remove $C_8$ and light aromatic hydrocarbons from acetone. Trays in the stripping section are necessary to effectively recover acetone and avoid significant product loss to bottoms. The effectiveness of removing $C_8$ hydrocarbons by the extractive distillation is due to $C_8$ volatility suppression. The relative volatilities of $iC_8$ to acetone (1 wt% $iC_8$ in crude acetone @760 mm Hg) as a function of $C_{10}$ solvent concentration in liquid are given below:

| $C_{10}$ Concentration in Liquid Wt. % | Relative Volatility $C_8$/acetone |
|---|---|
| 0 | 1.28 |
| 16.7 | 0.72 |
| 28.6 | 0.49 |
| 37.5 | 0.38 |
| 44.4 | 0.31 |
| 50.0 | 0.27 |
| 61.5 | 0.20 |
| 70.6 | 0.16 |
| 80.0 | 0.13 |

The bulk of the extractive distillation alkane solvent is recycled to column 23 from stripper 24 by means of line 12, make-up being added via line 32 and a purge removed via line 33. Substantially hydrocarbon free acetone is separated overhead via line 9 from extractive distillation column 23 and can be recovered as such or further treated.

Separated $C_8$ and light aromatic hydrocarbons are stripped from the extractive solvent alkane in stripper 24 and are separated overhead via line 11. As previously indicated, the extractive distillation solvent is recycled from stripper 24 to column 23 via line 12.

EXAMPLE

The following example illustrates the invention with reference to the drawing. Unless otherwise stated, all percentages are by weight.

A crude acetone stream from a propylene oxide and tertiary butyl alcohol process is treated in accordance with known procedures to separate light impurities, methanol and aldehydes; procedures such as are described above are employed.

A partially purified acetone stream comprised of acetone containing about 1% $C_8$ aliphatic hydrocarbon and about 700 ppm benzene impurities is obtained which is treated in accordance with the present invention. The partially purified acetone stream is fed at the rate of 100 parts per hour to the lower section (10th tray from the bottom) of column 23 via line 5. Column 23 has 40 theoretical trays.

$C_{10}$ alkane solvent is fed at the rate of 100 parts per hour to the upper section (30th tray from the bottom) of column 23 via line 12. An overhead stream of acetone which is essentially free of both $C_8$ aliphatic hydrocarbon and benzene is removed at the rate of 85 parts per hour via line 9, overhead conditions are 56° C. and atmospheric pressure. A bottoms stream is removed via line 10 at the rate of 115 parts per hour at 74°–75° C. and 0.5 psig. This stream contains essentially all of the $C_{10}$ alkane extractive distillation solvent and the $C_8$ and benzene impurities; as well as some acetone. The bottoms is sent to stripper 24 wherein the acetone, $C_8$ aliphatic hydrocarbon and benzene are stripped overhead and recovered via line 11, the $C_{10}$ alkane solvent is recovered via line 12 and recycled. A small purge may be taken via line 33 and make-up solvent added as needed via line 32.

This example illustrates the effective removal of close boiling aliphatic and aromatic impurities from acetone by the process of the invention.

We claim:

1. The method for the separation of $C_7$–$C_9$ hydrocarbon impurities from acetone which consists essentially of distilling a mixture of acetone and $C_7$–$C_9$ hydrocarbon impurities with a $C_9$–$C_{14}$ alkane and/or $C_8C_{12}$ aromatic hydrocarbon extractive distillation solvent and separating acetone reduced in $C_7$–$C_9$ hydrocarbon impurities overhead from a mixture of the $C_9$–$C_{14}$ alkane and/or $C_8$–$C_{12}$ aromatic hydrocarbon extractive distillation solvent and the $C_7$–$C_9$ hydrocarbon impurities.

2. The method of claim 1 wherein the extractive distillation solvent is a $C_9$–$C_{14}$ alkane.

3. The method of claim 1 wherein the extractive distillation solvent is a $C_8$–$C_{12}$ aromatic hydrocarbon.

4. The method of claim 1 wherein the acetone and impurities mixture is derived from the propylene oxide and tertiary butyl alcohol process.

* * * * *